United States Patent [19]

Miller

[11] Patent Number: 5,503,621
[45] Date of Patent: Apr. 2, 1996

[54] BODY BRACE

[75] Inventor: John J. Miller, Easton, Mass.

[73] Assignee: Boston Brace International, Inc., Avon, Mass.

[21] Appl. No.: 303,345

[22] Filed: Sep. 9, 1994

[51] Int. Cl.⁶ ..................................................... A61F 5/02
[52] U.S. Cl. ................... 602/19; 602/5; 602/18; 2/44; 2/45
[58] Field of Search .................... 602/18, 19, 5; 2/44, 45

[56] References Cited

U.S. PATENT DOCUMENTS

| 4,968 | 2/1847 | Knapp | 602/19 X |
|---|---|---|---|
| D. 186,642 | 11/1959 | Hale | 602/19 X |
| 2,060,173 | 11/1936 | Buschenfeldt | 602/19 |
| 2,332,119 | 10/1943 | Springer | 602/19 |
| 3,094,984 | 6/1963 | Jewett | 602/19 |
| 3,171,407 | 3/1965 | Rogers . | |
| 3,871,367 | 3/1975 | Miller . | |
| 4,202,327 | 5/1980 | Glancy . | |
| 4,493,393 | 1/1985 | Serber | 602/19 |
| 4,508,110 | 4/1985 | Modglin | 602/19 |
| 4,559,933 | 12/1985 | Batard et al. | 602/19 |
| 4,628,913 | 12/1986 | Lerman | 602/18 |
| 4,913,135 | 4/1990 | Mattingly | 602/18 |
| 4,957,103 | 9/1990 | Young et al. . | |
| 4,993,409 | 2/1991 | Grim | 602/19 |
| 5,000,169 | 3/1991 | Swicegood et al. . | |
| 5,012,798 | 5/1991 | Graf et al. . | |
| 5,039,247 | 8/1991 | Young et al. . | |
| 5,072,725 | 12/1991 | Miller . | |
| 5,074,288 | 12/1991 | Miller . | |
| 5,111,807 | 5/1992 | Spahn et al. . | |
| 5,158,531 | 10/1992 | Zamosky . | |
| 5,385,536 | 1/1995 | Burkhead et al. | 602/20 |

Primary Examiner—Richard J. Apley
Assistant Examiner—Kim M. Lee
Attorney, Agent, or Firm—Kriegsman & Kriegsman

[57] ABSTRACT

A body brace for use in the treatment of scoliosis and other spinal abnormalities includes a bottom shell sized and shaped to be fitted around a patient's pelvis, a middle shell sized and shaped to be fitted around the patient's abdomen and a top shell sized and shaped to be fitted around the back and the sides of the patient's rib cage. The top shell is made up of a left segment and a right segment. The middle shell is connected to the bottom shell by first and second lockable swivel mechanisms which provide for lateral, front and back, and rotational movement of the middle shell relative to the bottom shell. The left segment of the top shell is connected to the middle shell by a third lockable swivel mechanism which provides for lateral, front and back, and rotational movement of the left segment of the top shell relative to the middle shell independent of the right segment of the top shell. The right segment of the top shell is connected to the middle section by a fourth lockable swivel mechanism which provides for lateral, front and back, and rotational movement of the right segment of the top shell relative to the middle shell independent of the left segment of the top shell. Releasable fasteners are attached to the top, middle and bottom shells to assist in holding the brace in place on the patient's pelvis, abdomen and rib cage, respectively.

22 Claims, 5 Drawing Sheets

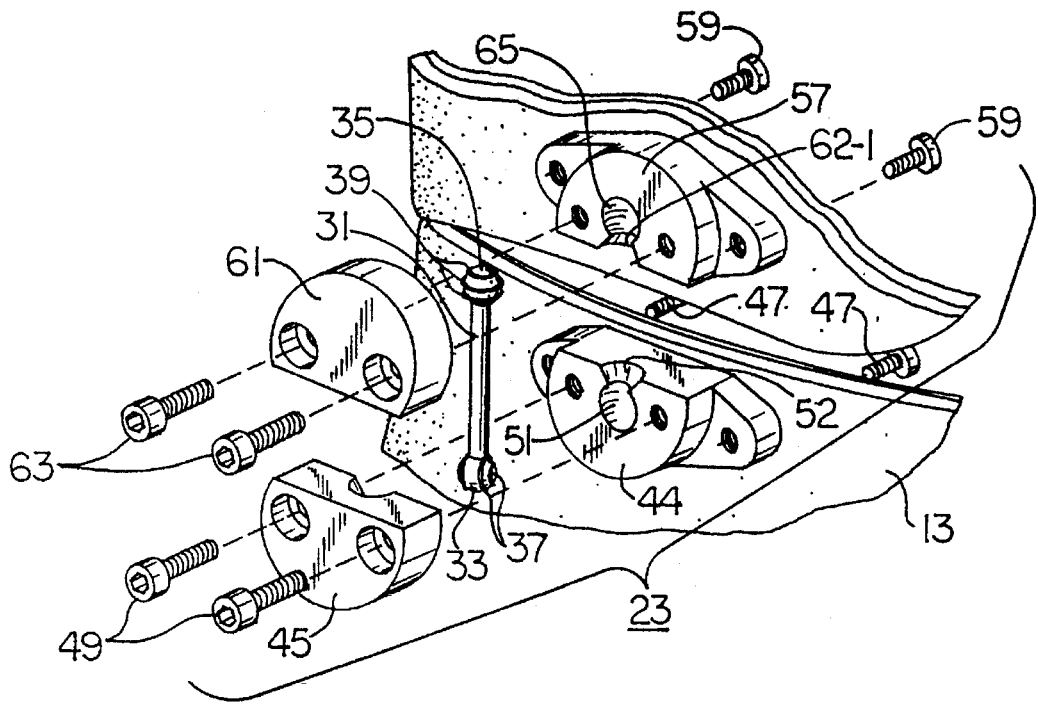
FIG. 4
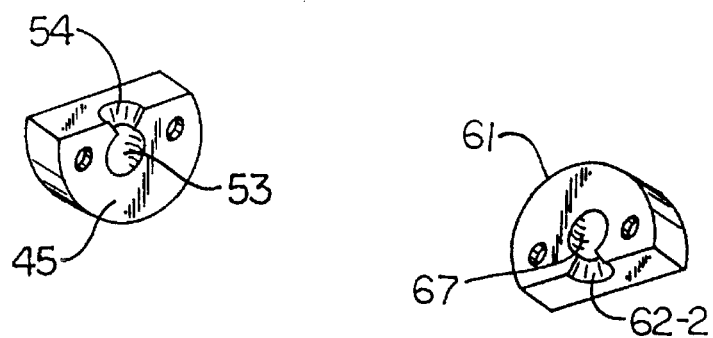
FIG. 5
FIG. 6

BODY BRACE

BACKGROUND OF THE INVENTION

The present invention relates generally to body braces and more specifically to a body brace for use in the treatment of scoliosis and other spinal abnormalities.

Body braces designed to treat scoliosis and other abnormal curvatures of the spine such as lordosis and kyphosis are known in the art.

In U.S. Pat. No. 3,871,367 to Miller there is disclosed a pelvic girdle comprising an outer layer of a hard substantially rigid plastic material and an inner layer of soft compressible plastic material bonded to the outer layer, the girdle being shaped to engage a person's pelvis and including an anterior and a vertically split posterior portion, the girdle having an upper anterior portion separated laterally from the remainder of the girdle and curving outwardly thereof, and connecting upper side portions on the girdle connecting the anterior and posterior portions thereof and including inwardly curved sections in both layers of the girdle for engaging the iliac crests of the wearer and which sections have appreciably thicker compressible inner layers thereon.

In U.S. Pat. No. 4,202,327 to Glancy there is disclosed a dynamic orthosis device which utilizes elastic forces to treat a patient who has scoliosis or other curvatures of the spine. The disclosed orthosis device includes first and second shell segments provided with a connecting arrangement for adjustibly aligning the segments so as to encompass the torso of the patient. At least one pressure pad is pivotally mounted to one of the shell segments, and an elastic strap is adjustably secured to one of the shell segments so as to exert a predetermined force on the pressure pad. The elastic strap, pressure pad and shell segments cooperate to apply adjustable dynamic forces to correct abnormal curvatures of the patient's spine.

In U.S. Pat. No. 5,012,798 to Graf et al there is disclosed a dynamic orthosis device for the tridimensional reduction of scoliosis. The dynamic orthosis device includes two elastically deformable plastic hands joined at the anterior of the device to laterally enclose the thorax of the patient. The hands assembly is connected to a pelvic girdle by at least two lateral supports made of elastically deformable semi-rigid material. As the rear of the hands, which are not attached, are expanded outward due to the movement of the thorax of the patient, the lateral supports provide a torsional return stress which forces the hands to create a pressure on the body of the patient. This pressure is beneficial in reeducating the spine of the patient and thereby reduces scoliosis.

In U.S. Pat. No. 5,158,531 to Zamosky there is disclosed a spinal orthosis which includes a continuous interior framework of ⅛" low density polyethylene sandwiched between layers of ¼" thick aliplast. The spinal orthosis also includes an anterior opening to provide cosmetic acceptability and independence of the user for placing on and removing the orthosis. A floating abdominal apron is provided to cover the anterior opening and the orthosis is devoid of joints and hinges to accomplish flexion and extension.

Other patents of interest include U.S. Pat. Nos. 5,111,807, 5,074,288, 5,072,725, 5,039,247, 5,000,169, 4,957,103, and 3,171,407.

SUMMARY OF THE INVENTION

It is an object of the present invention to provide a new and improved body brace for use in the treatment of scoliosis and other spinal abnormalities.

It is another object of the present invention to provide a body brace which can be used in the treatment of lateral, forward, backward, and rotational curvatures of both the upper and lower spine.

It is yet another object of the present invention to provide a body brace which can easily be placed on a patient and then removed when so desired.

It is still another object of the present invention to provide a body brace which can be mass produced and can be easily assembled.

In furtherance of the objects broadly set forth above, a body brace is provided which comprises a bottom shell sized and shaped to be fitted around a patient's pelvis, a middle shell sized and shaped to be fitted around the patient's abdomen, first and second swivel mechanisms for connecting the middle shell to the bottom shell, a top shell sized and shaped to be fitted around the back and the sides of the patient's rib cage, the top shell having left and right segments, and third and fourth swivel mechanisms for connecting the left and right segments, respectively, of the top shell to the middle shell, whereby, the bottom and top shells can each be positioned independent of the other relative to the middle shell.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate an embodiment of the invention and, together with the description, serve to explain the principles of the invention. In the drawings wherein like reference numerals represent like parts:

FIG. 4 is a fragmentary partially exploded perspective view of the body brace shown in FIG. 1;

FIG. 5 is a perspective view of one of the two plates of one of the swivel mechanisms shown in FIG. 4;

FIG. 6 is a perspective view of the other plate in the swivel mechanism shown partly in FIG. 5.

DETAILED DESCRIPTION OF A PREFERRED EMBODIMENT

Figure 1:
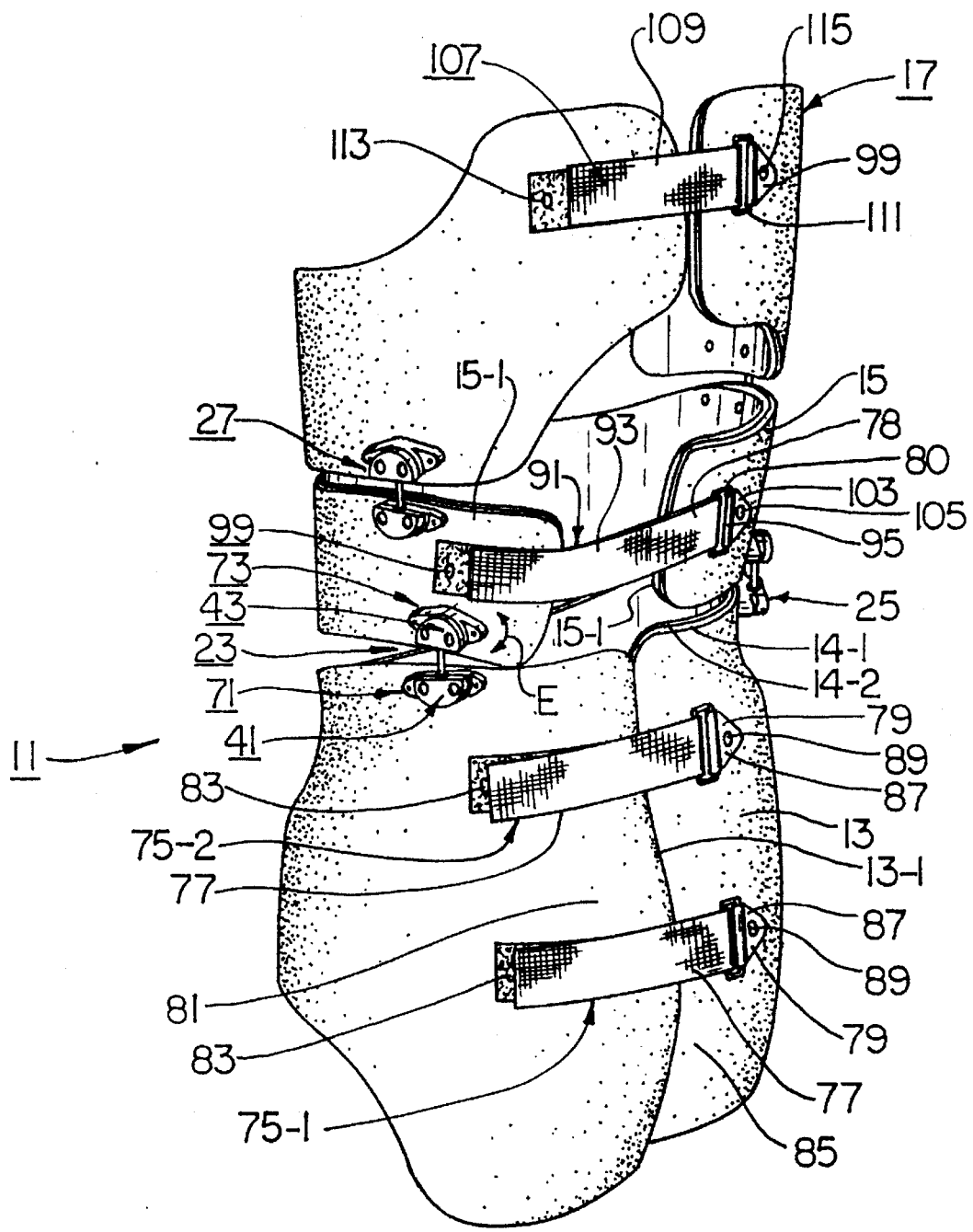
FIG. 1 is a rear perspective view of a body brace constructed according to the teachings of the present invention.
Figure 2:
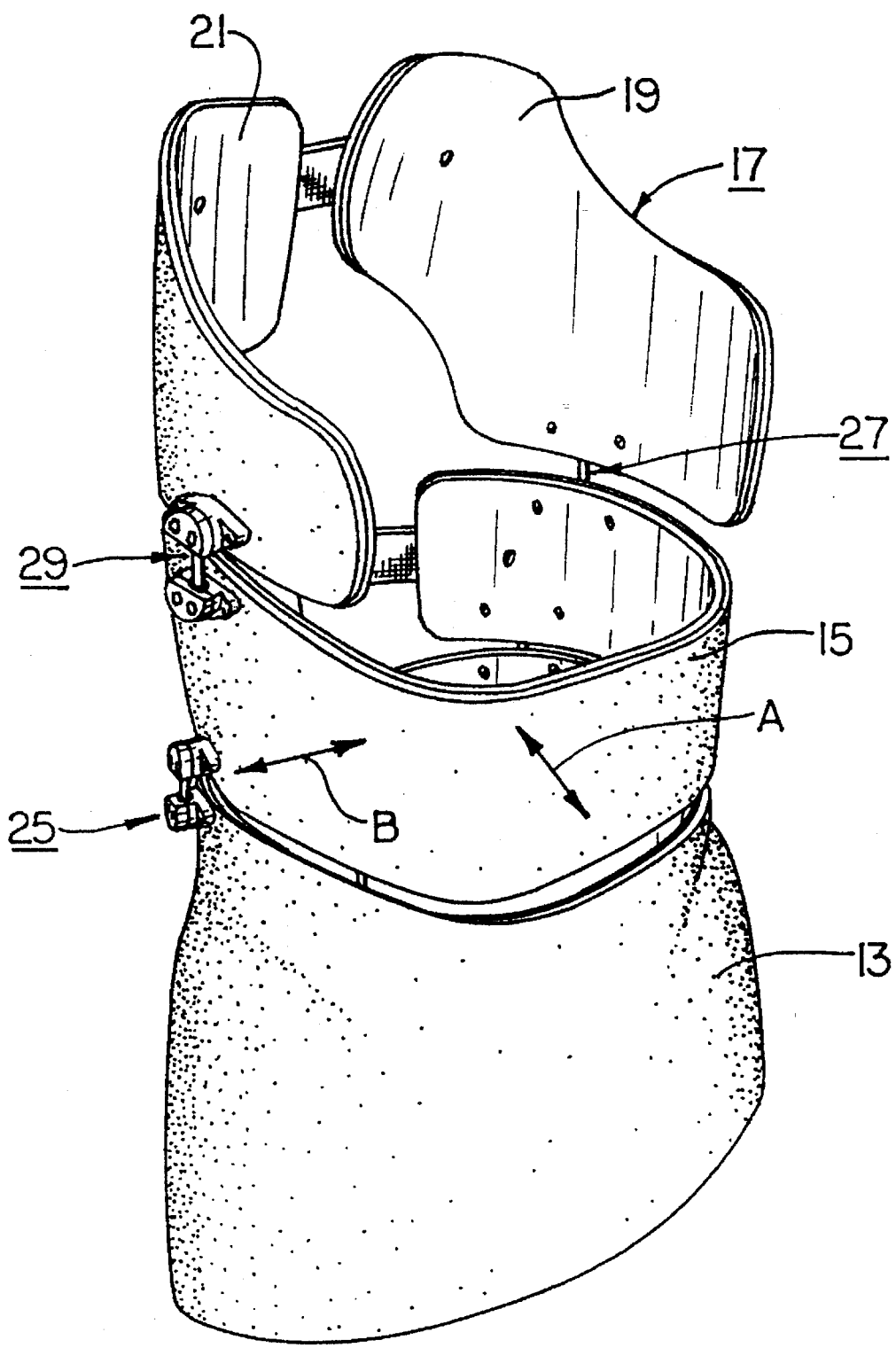
FIG. 2 is a front perspective view of the body brace shown in FIG. 1.
Figure 3:
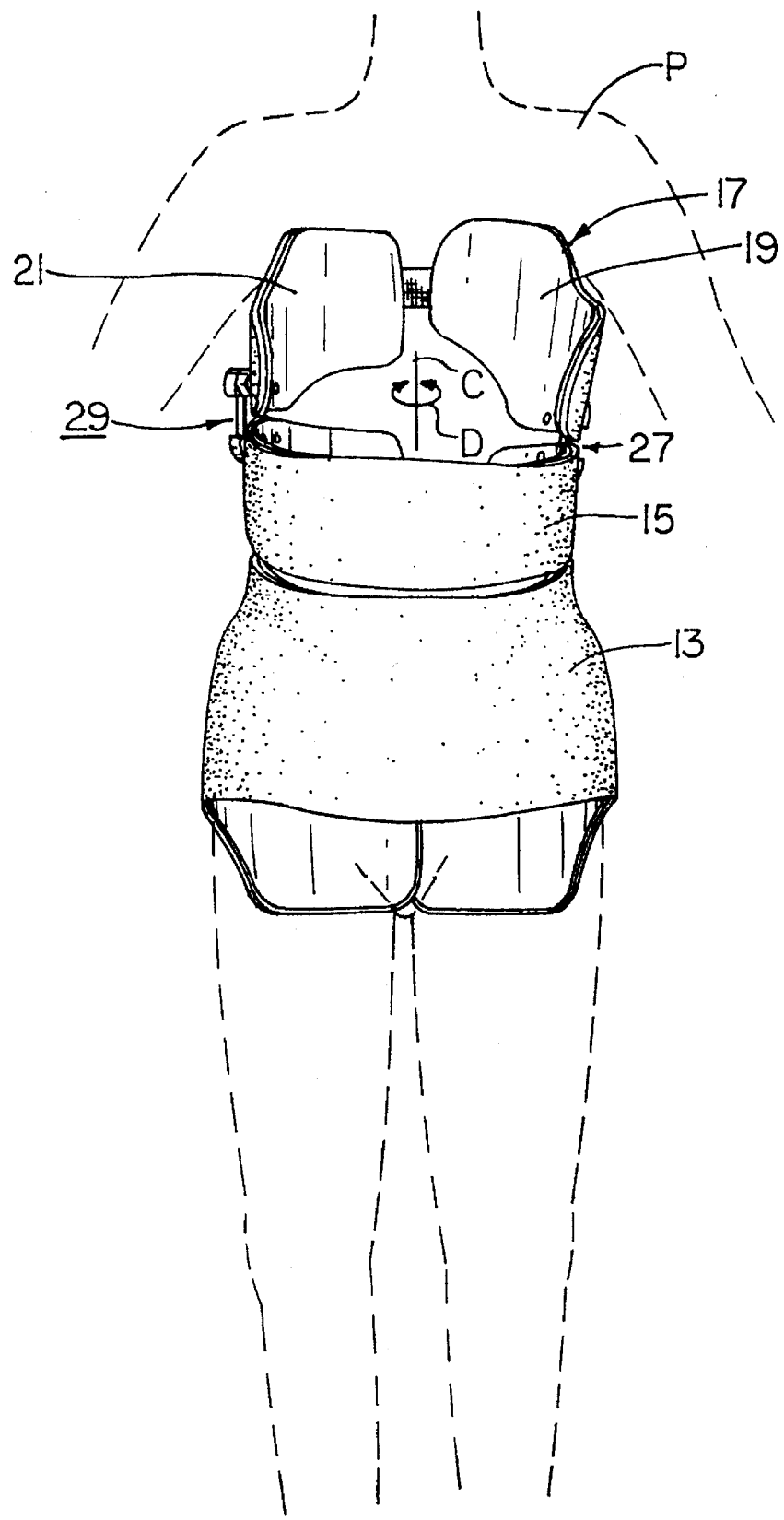
FIG. 3 is a front view of a patient wearing the body brace shown in FIG. 1.

Referring now to the drawings, there is shown in FIGS. 1 and 2 a body brace constructed according to the teachings of the present invention, the body brace being represented generally by reference numeral 11. In FIG. 3, body brace 11 is shown on a patient P.

Body brace 11 includes a bottom shell 13, a middle shell 15, and a top shell 17.

Bottom shell 13 is comprised of an outer layer 14-1 of a substantially rigid plastic material such as polypropylene and an inner layer 14-2 of a soft, compressible foam material such as polyurethane. Inner layer 14-2 is bonded to outer layer 14-1 over its entire surface thereof. Outer layer 14-1 may be about 1/8 to 3/16 inches thick and inner layer 14-2 may be about 3/16 to 1/4 inches thick. Middle shell 15 and top shell 17 are also each made of an outer layer of substantially rigid plastic material bonded to an inner layer of soft compressible foam material and each of the same thicknesses as bottom shell 13.

Bottom shell 13 is sized and shaped to be fitted around the patient's pelvis and includes a vertically split posterior portion 13-1 which serves to facilitate slipping the shell on and off the patient. Middle shell 15 is sized and shaped to be fitted around the patient's abdomen and has a vertically split posterior portion 15-1 which serves to facilitate slipping the shell on and off the patient. Top shell 17 is sized and shaped to be fitted around the back and the side of the patient's rib cage and comprises a left segment 19 and a right segment 21. Left segment 19 is intended to be positioned on the back and the side of the patient's left rib cage and right segment 21 is intended to be positioned on the back and the side of the patient's right rib cage.

Middle shell 15 is connected to bottom shell 13 by a first swivel mechanism 23 and a second swivel mechanism 25, one of swivel mechanisms 23 and 25 being on each side of body brace 11. First and second swivel mechanisms 23 and 25 together allow middle shell 15 to be moved frontwardly and backwardly relative to bottom shell 13 as shown by arrow A in FIG. 2, moved laterally relative to bottom shell 13 as shown by arrow B in FIG. 2 moved rotationally relative to bottom shell 13 about a vertical axis C as shown by arrow D in FIG. 3 and moved rotationally back and forth relative to bottom shell 13 as shown by arrow E in FIG. 1. First and second swivel mechanisms 23 and 25 are each lockable so that middle shell 15 can be fixed in place at a desired position relative to bottom shell 13.

Left segment 19 of top shell 17 is connected to middle shell 15 by a third swivel mechanism 27 and right segment 21 of top shell 17 is connected to middle shell 15 by a fourth swivel mechanism 29. Third swivel mechanism 27 allows left segment 19 to be moved frontwardly and backwardly, laterally, and rotationally about two perpendicular axis independent of right segment 21 and relative to middle shell 15. Fourth swivel mechanism 29 allows right segment 21 to be moved frontwardly and backwardly, laterally, and rotationally about two perpendicular axes and independent of left segment 19 relative to middle shell 15. Third and fourth swivel mechanisms 27, 29 are also each lockable so that the position of each segment of top shell 17 relative to middle shell 15 can be fixed.

First swivel mechanism 23 is made up of two interconnected ball and socket joints.

Referring also now to FIGS. 4, 5 and 6 first swivel mechanism 23 is shown in greater detail.

As can be seen, first swivel mechanism 23 comprises an elongated metal pin 31 constructed preferably of stainless steel and having a ball integrally formed at each end, the ball at one end being identified by reference numeral 33 and the ball at the other end being identified by reference numeral 35. Ball 33 includes a plurality of parallel ridges 37 on its surface to prevent slippage of ball 33 when in its socket (to be hereinafter described in greater detail). Similarly, ball 35 includes a plurality of parallel ridges 39 on its surface to prevent slippage of ball 35 when in its socket (to be hereinafter described in greater detail). Parallel ridges 37 are preferably orthogonal to parallel ridges 39 to prevent ridges 37 and 39 from wearing away in a relatively short period of time.

First swivel mechanism 23 further comprises a pair of sockets 41 and 43. Socket 41 comprises a bracket 44 and a plate 45. Bracket 44 is secured to bottom shell 13 by a pair of screws 47 and plate 45 is secured to bracket 44 by a pair of screws 49. Bracket 44 has a hemispherical cavity 51 and a bevelled recess 52 and plate 45 has a hemispherical cavity 53 and a bevelled recess 54. Cavities 51 and 53 together form a spherical cavity into which ball 33 is disposed and recesses 52 and 54 form an opening for pin 31. The bevels enable wide movement of pin 31. By tightening screws 49, ball 33 can be locked in place in socket 41. Socket 43 includes a bracket 57 which is secured to middle shell 15 by a pair of screws 59 and a plate 61 which is secured to bracket 57 by a pair of screws 63. Bracket 57 has a hemispherical cavity 65 which together with a hemispherical cavity 67 on plate 61 form a spherical cavity into which ball 35 is disposed. Ball 35 can be locked in place in socket 49 by tightening screws 63. Bracket 57 and plate 61 also have bevelled recesses 62-1 and 62-2.

Socket 41 and ball 33 together create a first ball-and-socket joint 71, while socket 69 and ball 35 together form a second ball and socket joint 73.

Second, third and fourth swivel mechanisms 25, 27 and 29 are identical in construction to swivel mechanism 23.

First and second releasable fastener assemblies 75-1 and 75-2 are fixedly attached to split posterior portion 13-1 of shell 13 to assist in holding bottom shell 13 in place around the patient's pelvis. Each fastener assembly 75-1 and 75-2 includes a VELCRO hook and loop type fastener strap 77 and a buckle 79. Fastener straps 77 are attached to one side 81 of posterior portion 13-1 by rivets 83. Buckles 79 are attached to the other side 85 of posterior portion 13-1 through chafes 87 by rivets 89.

A third releasable fastener assembly 91 is fixedly attached to split posterior portion 15-1 of shell 15 to assist in holding middle shell 15 in place around the patient's abdomen. Fastener assembly 91 includes a VELCRO hook and loop type fastener strap 93 and a buckle 95. Fastener strap 93 is attached to one side 97 of posterior portion 15-1 by a rivet 99. Buckle 95 is attached to the other side 101 of posterior portion 15-1 through a chafe 103 by a rivet 105.

A fourth releasable fastener assembly 107 is provided for assisting in holding left segment 19 and right segment 21 in position around the back and side of the patient's left rib cage and right rib cage, respectively. Fastener assembly 107 includes a VELCRO hook and loop type fastener strap 109 and a buckle 111. Fastener strap 109 is attached to left segment 19 by a rivet 113. Buckle 95 is attached to right segment 21 through a chafe 115 by a rivet 117.

Body brace 11 may be used in the following manner.

First, the two fastener straps 77 and fastener straps 93 and 109 and the screws in each socket which secure the plate to its associated bracket are loosened. Body brace 11 is then placed on the patient so that bottom shell 13 is positioned properly around the patient's pelvis. Middle shell 15 is then positioned properly around the patient's abdomen. Finally, left segment 19 and right segment 21 of top shell 17 are positioned properly around the back and the side of the patient's left and right rib cage, respectively. Once bottom, middle and top shells 13, 15 and 17 are properly positioned on the patient, the straps in fastener assemblies 75-1, 75-2, 91 and 107 are secured, thereby fixing the position of shells 13, 15 and 17 on the patient.

Middle shell 15 is then moved frontwardly or backwardly, and/or laterally and/or rotationally relative to bottom shell 13, as necessary, to meet the patient's needs. Middle shell 15 is intended to be displaced relative to bottom shell 13 in such a direction so as to counteract the curvature of the patient's lower spine. Once middle shell 15 is positioned properly relative to bottom shell 13 screws 49 and 63 in first and second swivel mechanisms 23 and 25 are tightened, thereby locking middle shell 15 in place relative to bottom shell 13.

Left segment 19 of top shell 17 is then moved frontwardly or backwardly, and/or laterally, and/or rotationally independent of right segment 21 relative to middle shell 13, as necessary, to meet the patient's needs. Left segment 19 is intended to be displaced relative to middle shell 15 in such a direction so as to counteract the curvature of the patient's upper spine. Once left segment 19 is positioned properly relative to middle shell 15, screws 49 and 63 from third swivel mechanism 27 are tightened, thereby locking the position of left segment 19 relative to middle shell 15. It should be noted that left segment 19 can be moved independent of right segment 21 relative to middle shell 15 so as to counteract sharp curves of the upper spine.

Right segment 21 of top shell 17 is then moved frontwardly or backwardly, and/or laterally, and/or rotationally independent of left segment 19 relative to middle shell 13 as necessary to meet the patient's needs. Right segment 21 is intended to be displaced relative to middle shell 15 in such a direction so as to counteract the curvature of the patient's upper spine. Once right segment 21 is positioned properly relative to middle shell 15 screws 49 and 63 from fourth swivel mechanism 29 are tightened, thereby locking the position of right segment 21 relative to middle shell 15. It should also be noted that right segment 21 can be moved independent of left segment 19 relative to middle shell 15 so as to counteract sharp curves of the upper spine.

Body brace 11 can be removed from the patient when desired by loosening fastener straps 77, 93 and 109. Also, the position of shells 13, 15, and 17 relative to each other can be readjusted on the patient at any time by simply loosening the screws securing the plates to the brackets in swivel mechanisms 23, 25, 27 and 29.

Figure 7:
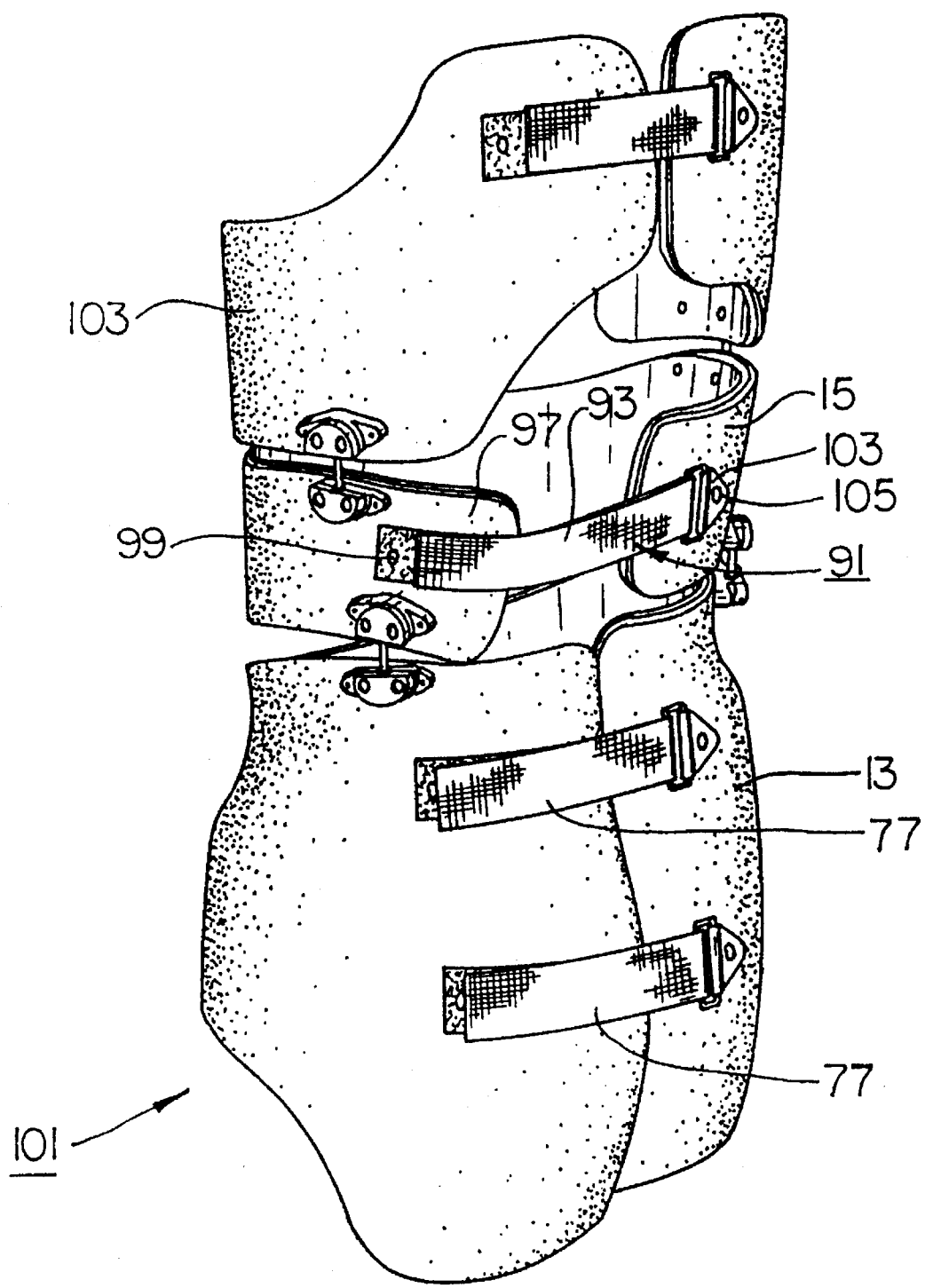
FIG. 7 is a rear perspective view of another embodiment of a body brace constructed according to the teachings of the present invention.

In FIG. 7 is shown an embodiment of the invention 101 in which the top shell 103 is a single piece rather than two segments as in the FIG. 1 embodiment.

The embodiments of the present invention described above are intended to be merely exemplary and those skilled in the art shall be able to make numerous variations and modifications to it without departing from the spirit of the present invention. For example, locking mechanisms which are separate from the swivel mechanisms may be employed. All such variations and modifications are intended to be within the scope of the present invention as defined in the appended claims.

What is claimed is:

1. A body brace for use in the treatment of scoliosis and other spinal abnormalities comprising:

a) a bottom shell sized and shaped to be fitted around a patient's pelvis;

b) a middle shell sized and shaped to be fitted around the patient's abdomen;

c) first and second swivel mechanisms for connecting said middle shell to said bottom shell;

d) a top shell sized and shaped to be fitted around the back and sides of the patient's rib cage;

e) third and fourth swivel mechanisms for connecting said top shell to said middle shell; and f) whereby said bottom and top shells can each be adjusted independent of the other relative to said middle shell.

2. The body brace as claimed in claim 1 wherein each of said first, second, third, and fourth swivel mechanisms are lockable.

3. The body brace as claimed in claim 1 wherein one of said first or second swivel mechanisms is lockable.

4. The body brace as claimed in claim 1 wherein either said third or fourth swivel mechanisms is lockable.

5. The body brace as claimed in claim 1 and further including fastening means to assist in holding said bottom shell in place on the patient.

6. The body brace as claimed in claim 5 wherein said fastening means comprises a strap of hoop and loop pile fasteners and a buckle.

7. The body brace as claimed in claim 1 and further including fastening means to assist in holding said middle shell in place on the patient.

8. The body brace as claimed in claim 6 wherein said fastening means comprises a strap of hoop and loop pile fasteners and a buckle.

9. The body brace as claimed in claim 1 and further including fastening means to assist in holding said top shell in place on the patient.

10. The body brace as claimed in claim 7 wherein said fastening means comprises a strap of hoop and loop pile fasteners and a buckle.

11. The body brace as claimed in claim 1 wherein said top shell further comprises a left segment and a right segment, said left segment not being integrally formed with said right segment.

12. The body brace as claimed in claim 11 wherein said third swivel mechanism connects said left segment to said middle shell and said fourth swivel mechanism connects said right segment to said middle shell.

13. The body brace as claimed in claim 11 wherein said left segment can be adjusted independent of said right segment relative to said middle shell.

14. The body brace as claimed in claim 11 wherein said right segment can be adjusted independent of said left segment relative to said middle shell.

15. The body brace as claimed in claim 1 wherein said first and second swivel mechanisms are constructed to provide for lateral, front and back, and rotational movement of said middle shell relative to said bottom shell.

16. The body brace as claimed in claim 1 wherein said third and fourth swivel mechanisms are constructed to provide for lateral, front and back, and rotational movement of said top shell relative to said middle shell.

17. The body brace as claimed in claim 1 wherein either said first or second swivel mechanisms are constructed to provide for lateral, front and back, and rotational movement of said middle shell relative to said bottom shell.

18. The body brace as claimed in claim 1 wherein either said third or fourth swivel mechanisms are constructed to provide for lateral, from and back, and rotational movement of said top shell relative to said middle shell.

19. The body brace as claimed in claim 1 wherein said first, second, third, and fourth swivel mechanisms each comprise an elongated pin having a ball at each end and a pair of sockets, each of said pair of balls being mounted in one of said sockets.

20. The body brace as claimed in claim 19 wherein each of said sockets comprises a bracket and a plate.

21. A body brace for use in treating a human patient having scoliosis, said body brace comprising:
   a) a bottom shell sized and shaped to be fitted around a patient's pelvis;
   b) a top shell sized and shaped to be fitted around the back and sides of a patient's rib cage;
   c) a swivel mechanism for connecting said top shell to said bottom shell so that said top shell can be swivelled relative to said bottom shell, said swivel mechanism comprising a pair of ball and socket joints, one of said ball and socket joints being associated with said bottom shell, the other said ball and socket joint being associated with said top shell.

22. A body brace for use in treating a human patient having scoliosis, said orthopedic body brace comprising:
   a) a bottom shell sized and shaped to be fitted around a patient's pelvis;
   b) a middle shell sized and shaped to be fitted around the patient's abdomen;
   c) a top shell sized and shaped to be fitted around the back and sides of the patient's rib cage;
   d) a mechanism for swivelly connecting said middle shell to said bottom shell; and
   e) a mechanism for swivelly connecting said top shell to said middle shell.

* * * * *